United States Patent [19]
Scharwächter et al.

[11] 4,358,458
[45] Nov. 9, 1982

[54] TERTIARY IMIDAZOLYL ALCOHOLS AND METHOD FOR THE TREATMENT OF GENERALIZED AND LOCAL INFECTIONS CAUSED BY FUNGI AND YEASTS

[75] Inventors: Peter Scharwächter, Moorrege; Klaus Gutsche, Rellingen; Wilhelm Kohlmann, Moorrege; York Hartleben, Heist; Wolfgang Heberle, Appen, all of Fed. Rep. of Germany

[73] Assignee: Nordmark-Werke GmbH, Uetersen, Fed. Rep. of Germany

[21] Appl. No.: 796,613

[22] Filed: May 13, 1977

[30] Foreign Application Priority Data

May 22, 1976 [DE] Fed. Rep. of Germany ....... 2623129

[51] Int. Cl.³ ................... A61K 31/415; C07D 233/60
[52] U.S. Cl. ................................... 424/273 R; 548/341
[58] Field of Search ..................... 548/341; 424/273 R

[56] References Cited
U.S. PATENT DOCUMENTS 3,658,813  4/1972  Godefroi et al. ............... 548/341 X
3,679,697  7/1972  Kreider et al. ..................... 548/341
3,839,574 10/1974  Godefroi et al. ............... 548/341 X

OTHER PUBLICATIONS

Cooper et al., Chemical Abstracts, vol. 84, (1976), 180,131j.

Primary Examiner—Richard Raymond
Attorney, Agent, or Firm—Pearne, Gordon, Sessions, McCoy & Granger

[57] ABSTRACT

The present invention is directed to new tertiary imidazolyl alcohols having the general formula (I)

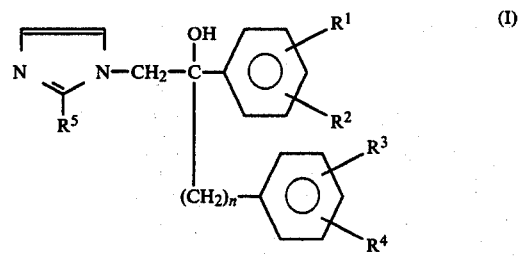

and to their pharmacologically acceptable acid addition salts with usual acids. The invention is further directed to a method for the treatment of generalized and local infections caused by fungi or yeasts by administering to a mammal suffering from such a disease a compound of the general formula (I) orally or externally in a suitable pharmaceutical preparation.

17 Claims, No Drawings

TERTIARY IMIDAZOLYL ALCOHOLS AND METHOD FOR THE TREATMENT OF GENERALIZED AND LOCAL INFECTIONS CAUSED BY FUNGI AND YEASTS

This invention relates to new imidazole compounds corresponding to the general formula

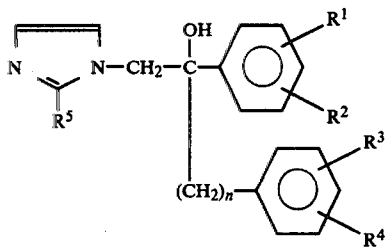

in which $R^1$, $R^2$, $R^3$ and $R^4$, which may be the same or different, represent hydrogen atoms, halogen atoms, lower alkyl groups with 1 to 4 carbon atoms or lower alkoxy groups with 1 to 4 carbon atoms, $R^5$ represents hydrogen or a lower alkyl group with 1 to 3 carbon atoms and n is an integer of 0 or 1,
and to their pharmacologically compatible acid addition salts with the usual acids. In formula (I) above, halogen is preferably fluorine, chlorine and bromine.

Preferred compounds of formula (I) are those in which $R^1$, $R^2$, $R^3$ and $R^4$, which may be the same or different, represent hydrogen atoms, halogen atoms, lower alkyl groups with 1 to 4 carbon atoms or lower alkoxy groups with 1 to 4 carbon atoms, $R^5$ represents hydrogen or a lower alkyl group with 1 to 3 carbon atoms and n is the number 1, and their pharmacologically compatible acid addition salts with the usual acids. In this case, too, halogen is preferably fluorine, chlorine and bromine. These compounds correspond to the general formula

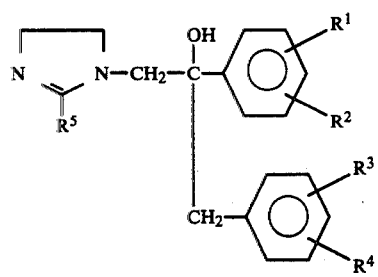

Among the compounds of formula (II), those in which $R^1$, $R^2$, $R^3$ and $R^4$, which may be the same or different, represent hydrogen, fluorine, bromine, methyl or methoxy, and $R^5$ represents hydrogen, are particularly preferred by virtue of their particularly favourable properties, although the greatest preference is attached to those compounds of formula (II) in which the substituents $R^1$ and $R^3$ are each in the 4-position to the alkylene chain, so that they correspond to the general formula

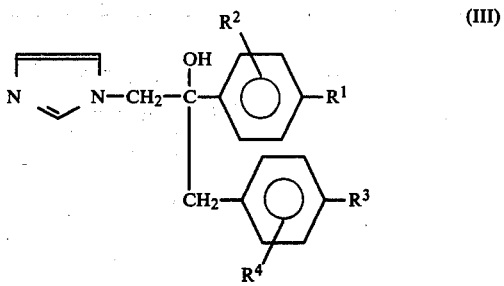

and their pharmacologically compatible acid addition salts with the usual acids.

Usual acids for the formation of pharmacologically compatible salts are, in particular, nitric acid, hydrochloric acid, sulphuric acid, phosphoric acid, acetic acid, propionic acid, lactic acid, succinic acid, tartaric acid, citric acid, benzoic acid, salicyclic acid and nicotinic acid. However, it is preferred to use the above-mentioned inorganic acids, especially nitric acid or hydrochloric acid, which form salts that crystallise particularly well with the compounds according to the invention.

Formula (II) shows that the carbon atom to which the hydroxyl group is attached is asymmetrical so that the separation and isolation or production of a certain optical isomer can be carried out in accordance with generally known principles (Houben-Weyl, Methoden der organischen Chemie, 1955, Vol. 4/2; E. L. Eliel, Stereochemie der Kohlenwasserstoffverbindungen, 1966). These optical isomers and their production are covered by the present invention.

The compounds of formula (I) and their salts show excellent chemotherapeutic and, in particular, antimycotic and antibacterial activity. These properties enable these new compounds to be used as medicaments, especially for the treatment of mycosis and particularly for the oral or local treatment of generalized or local infections caused by fungi and yeasts in human and veterinary medicine. For oral treatment they are administered in the form of for instance dragees, juices, capsules or tablets, and this in a dosage ranging from 0.5 to 100 mg./kg. of body weight of the mammal to be treated. For external use they are applied in the form of ointments, cremes, emulsions, solutions or powders containing 0.1 to 10% by weight of the active compound. The pharmaceutical preparations further contain usual pharmaceutical additives, carriers and auxiliary agents.

The antimicrobial activity of the compounds corresponding to general formula (I) in vitro was tested in a series dilution test with dilution ratios of from 1:10,000 to 1:200,000 against the germs Staphylococcus aureus, Trichophyton mentagrophytes and Candida albicans. The result of a selection is shown in Table 1.

The results were evaluated by the following graduations of the growth inhibition level:
 φ=complete inhibition
 (+)=strong inhibition
 +=moderate inhibition
 ++=slight inhibition
 +++=no inhibition
The following dilution ratios were selected as the dilution ratio V:
 a=1:10,000
 b=1:100,000
 c=1:200,000

TABLE 1

$$\text{(I)}$$

[Structure: Imidazole-N-CH₂-C(OH)(phenyl-R¹,R²)-(CH₂)ₙ-phenyl-R³,R⁴; imidazole has R⁵ substituent]

| n | R¹ | R² | R³ | R⁴ | R⁵ | Salt | D | Staph. aureus | Trichoph. mentag. | Candida albicans |
|---|----|----|----|----|----|----|---|---------------|-------------------|------------------|
| 0 | 3-Cl | H | 3-Cl | H | H |  | a | φ | φ | (+) |
|   |      |   |      |   |   |  | b | +++ | ++ | +++ |
|   |      |   |      |   |   |  | c |   |   |   |
| 1 | H | H | 4-Cl | H | H | .HNO₃ | a | φ | φ | (+) |
|   |   |   |      |   |   |       | b | +++ | +++ | +++ |
|   |   |   |      |   |   |       | c |   |   |   |
| 1 | 4-Cl | H | H | H | H | .HNO₃ | a | +++ | (+) | φ |
|   |      |   |   |   |   |       | b |     | +++ | +++ |
|   |      |   |   |   |   |       | c |     |     |     |
| 1 | H | H | 2-Cl | 4-Cl | H | .HNO₃ | a | +++ | φ | (+) |
|   |   |   |      |      |   |       | b |     | + | +++ |
|   |   |   |      |      |   |       | c |   |   |   |
| 1 | 2-Cl | 4-Cl | H | H | H | .HNO₃ | a | φ | φ | φ |
|   |      |      |   |   |   |       | b | φ | φ | (+) |
|   |      |      |   |   |   |       | c |   |   |   |
| 1 | 4-Cl | H | 4-Cl | H | H | .HNO₃ | a | φ | φ | φ |
|   |      |   |      |   |   |       | b | + | ++ | +++ |
|   |      |   |      |   |   |       | c |   |   |   |
| 1 | 2-Cl | 4-Cl | 4-Cl | H | H | .HCl | a | φ | φ | φ |
|   |      |      |      |   |   |      | b | φ | φ | φ |
|   |      |      |      |   |   |      | c |   | φ | (+) |
| 1 | 2-Cl | 4-Cl | 2-Cl | 4-Cl | H | .HNO₃ | a | φ | φ | φ |
|   |      |      |      |      |   |       | b | φ | φ | φ |
|   |      |      |      |      |   |       | c |   | φ | (+) |
| 1 | 2-Cl | 4-Cl | 4-CH₃ | H | H | .HNO₃ | a | φ | φ | φ |
|   |      |      |       |   |   |       | b | φ | φ | φ |
|   |      |      |       |   |   |       | c |   |   |   |
| 1 | 2-CH₃ | 4-Cl | 2-Cl | H | H | .HNO₃ | a | φ | φ | φ |
|   |       |      |      |   |   |       | b | φ | φ | (+) |
|   |       |      |      |   |   |       | c |   |   |   |
| 1 | 4-Br | H | 4-Cl | H | H | .HNO₃ | a | φ | φ | φ |
|   |      |   |      |   |   |       | b | φ | (+) | (+) |
|   |      |   |      |   |   |       | c |   |   |   |
| 1 | 4-OCH₃ | H | 3-Cl | 4-Cl | H | .HNO₃ | a | φ | φ | φ |
|   |        |   |      |      |   |       | b | φ | +++ | (+) |
|   |        |   |      |      |   |       | c |   |   |   |
| Miconazol | 1-(2,4-dichloro-β-(2,4-dichloro-benzyloxy)-phenethyl)-imidazole nitrate | | | | | | a | φ | φ | φ |
|           |                                                                          | | | | | | b | φ | φ | (+) |
|           |                                                                          | | | | | | c |   | (+) |   |

For equally good and, in some cases, better activities against fungi, yeasts and bacteria in the test-tube dilution test, the new compounds of general formula (I) have proved in vivo to be distinctly superior to the imidazole derivative, MICONAZOL (1-[2,4-dichloro-β-(2,4-dichlorobenzyloxy)-phenethyl]imidazole nitrate), recently introduced into medicinal practice as antimycotics in animal tests, for example on Candida-infected mice.

Accordingly, the compounds according to the invention are particularly suitable for the oral treatment of generalised infections caused by fungi and yeasts in human and veterinary medicine. Since the hitherto available curatives are unsatisfactory (Lit.: Infection 2, 95 (1974); Chemotherapy 22, 211 (1976), the new compounds of formula (I) represent a genuine enrichment of medicinal resources. In addition, they may be used equally well for example for the local treatment of superficial infections and of infections of the mucosa accessible to local treatment. The compounds may be used either individually or in combination with other known active principles in this field, such as antibacterially active compounds, especially antibiotics.

In order to determine oral activity, groups of 10 mice weighing approximately 20 g were pretreated for 2 days with intramuscular doses of 50 mg/kg of hydrocortisone in order to obtain firm rooting of the infection. The mice were then each infected intravenously with 500,000 Candida albicans germs and subsequently treated orally twice a day for 7 days with 100 mg/kg of the substance to be tested. In addition to an infected, but untreated control group, another group was treated for comparison with the comparison substance MICONAZOL.

Table 2 shows the outcome of a selection of these tests. As can be seen from these results, up to 100% of the animals treated with the new compounds were still alive on the last day of the treatment, whilst in the control group and in the group treated with MICONAZOL only 20% of the animals were still alive.

The $LD_{50}$-values increased by approximately the factor 2 over the comparison substance show another advantage of the new compounds.

TABLE 2

| Substance | \multicolumn{7}{c|}{Number of Animals surviving on the ... day after infection Day} | $LD_{50}$ (mice) |
|---|---|---|---|---|---|---|---|---|
| | 1 | 2 | 3 | 4 | 5 | 6 | 7 | |
| A | 10 | 10 | 10 | 10 | 10 | 10 | 10 | 1000 mg/kg |
| B | 10 | 10 | 10 | 10 | 10 | 10 | 10 | 1000 mg/kg |
| C | 10 | 10 | 10 | 10 | 10 | 10 | 9 | 1000 mg/kg |
| D | 10 | 10 | 10 | 10 | 10 | 10 | 9 | not determined |
| E | 10 | 10 | 10 | 10 | 10 | 10 | 10 | not determined |
| F | 10 | 10 | 10 | 10 | 10 | 10 | 9 | not determined |
| MICONAZOL | 10 | 10 | 8 | 8 | 6 | 4 | 2 | 578 mg/kg (Lit.) |
| Control | 10 | 9 | 5 | 2 | 2 | 2 | 2 | |

A = 1,2-bis-(4-chlorophenyl)-3-(imidazol-1-yl)-propan-2-ol nitrate
B = 1-(4-chlorophenyl)-2-(2,4-dichlorophenyl)-3-(imidazol-1-yl)-propan-2-ol hydrochloride
C = 1,2-bis-(2,4-dichlorophenyl)-3-(imidazol-1-yl)-propan-2-ol nitrate
D = 1-(2,4-dichlorophenyl)-2-phenyl-3-(imidazol-1-yl)-propan-2-ol nitrate
E = 1-(4-chlorophenyl)-2-phenyl-3-(imidazol-1-yl)-propan-2-ol nitrate
F = 1-phenyl-2-(4-chlorophenyl)-3-(imidazol-1-yl)-propan-2-ol nitrate.

The new compounds may be used either as such or in combination with inert, non-toxic, pharmaceutically compatible, solid, semi-solid or liquid excipients. They may be made up in the form of tablets, dragees, capsules, pills, granulates, suppositores, aqueous solutions, suspensions and emulsions, optionally sterile injectable solutions, non-aqueous emulsions, suspensions and solutions, syrups, ointments, creams, pastes, lotions, etc.

The therapeutically active compound is preferably present in pharmaceutical preparations in a concentration of from 0.5 to 90% by weight, based on the total mixture.

The new tertiary alcohols of general formula (I) and their acid addition salts may be produced by reacting a compound corresponding to the general formula

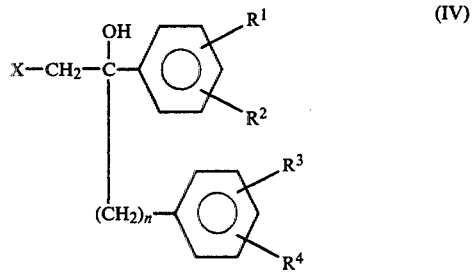
(IV)

in which $R^1$, $R^2$, $R^3$, $R^4$ and n are as defined above and X represents halogen, preferably chlorine or bromine, with an imidazole corresponding to the general formula

(V)

in which $R^5$ is as defined above, optionally in the presence of an acid-binding agent or in the form of one of its alkali salts, as obtained for example by treatment with sodium methylate in a suitable solvent, and optionally converting the compound obtained into a pharmacologically compatible acid addition salt with an acid of the type usually employed for this purpose.

The reaction of the halogen compounds (IV) with imidazoles corresponding to formula (V) or their alkali salts may be carried out both in the presence and in the absence of diluents. The diluents used are primarily organic solvents, for example dimethyl formamide, hexamethyl phosphortriamide, acetonitrile and benzene.

Unless an alkali salt of the imidazole (V) is used, the reaction according to the invention is preferably carried out in the presence of an excess of an acid-binding agent, but at least in the presence of approximately the stoichiometrically necessary quantity of an acid-binding agent. It is preferred to use an excess of the imidazole of formula (V) used as the acid-binding agent. Other suitable binding agents are any of the usual acid-binding agents such as, for example, hydroxides, carbonates and alcoholates of alkali and alkaline earth metals and also organic bases, such as tertiary amines.

The reaction temperatures may be varied over a relatively wide range. In general, the reaction is carried out at temperatures of from 0° to 150° C. and is preferably carried out at temperatures of from 30° to 120° C.

The compounds of general formula (IV) hitherto unreported in the literature may be produced in known manner, for example by the methods employed for producing tertiary alcohols from the corresponding ketones or carboxylic acid derivatives and Grignard compounds (Lit.: Houben-Weyl, Methoden der organischen Chemie, 13/2a, 46–527 (1973).

Compounds of formula (IV) are obtained, for example, by reacting a ketone corresponding to the general formula

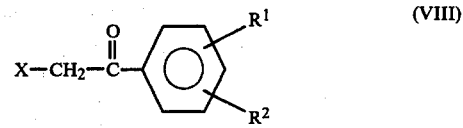
(VIII)

in which $R^1$, $R^2$ and X are as defined above, with a Grignard compound corresponding to the general formula

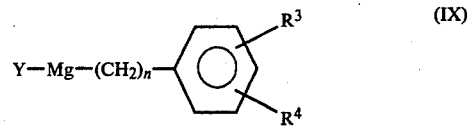
(IX)

in which $R^3$, $R^4$ and n are as defined above and Y represents halogen, preferably chlorine or bromine, in one of the solvents normally used for Grignard reactions, preferably diethylether or tetrahydrofuran.

Compounds of formula (IV) in which n=0 and the substituent pairs $R^1/R^2$ and $R^3/R^4$ are identical, are obtained by reacting a halogen carboxylic acid ester corresponding to the general formula

(VI)

in which X represents halogen, preferably chlorine or bromine, and $R^6$ is preferably an alkyl radical with 1 to 4 carbon atoms, with at least twice the stoichiometrically necessary quantity of a Grignard compound corresponding to the general formula

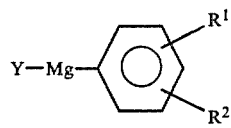

in which $R^1$ and $R^2$ are as defined above and Y represents halogen, preferably chlorine or bromine, in one of the solvents normally used for Grignard reactions, preferably diethyl ether or tetrahydrofuran.

The compounds of general formula (IV) are generally not isolated, but are reacted after their production with an imidazole of formula (V) as described above. In special cases, however, the compounds of formula (IV) may be isolated and subsequently reacted with an imidazole of formula (V) in the manner described which can be of advantage for obtaining higher yields.

EXAMPLE 1

15 g of magnesium chips are reacted with 94.2 g of bromobenzene in 250 ml of absolute ether at 30° to 35° C., followed by the dropwise addition over a period of 30 minutes at 0° to 10° C. of 24.5 g of chloroacetic acid ethyl ester. After stirring for 1 hour, the reaction mixture is poured onto ice, acidified with dilute hydrochloric acid and extracted by shaking with methylene chloride. The organic phase is washed twice with water, subsequently dried over sodium sulphate and concentrated in vacuo. The oily residue is distilled in a high vacuum at 135°-140° C./0.03 Torr. 2-Chloro-1,1-diphenyl-ethan-1-ol melting at 64° to 66° C. is obtained in a yield of 32.8 g.

2 g of imidazole are dissolved in 25 ml of dimethyl formamide and 1.6 g of sodium methylate added to the resulting solution. 7 g of 2-chloro-1,1-diphenyl-ethan-1-ol dissolved in dimethyl formamide are added dropwise to the solution at 10° to 15° C., followed by stirring for 2 hours at 100° C. After cooling, the sodium chloride precipitated is filtered off and the reaction product concentrated in vacuo. 4.5 g of 1,1-diphenyl-2-(imidazol-1-yl)-ethan-1-ol melting at 208° to 210° C. crystallise out of the residue following the addition of ethanol.

EXAMPLES 2 AND 3

The following compounds were produced as in Example 1:
1,1-bis-(3-chlorophenyl)-2-(imidazol-1-yl)-ethan-1-ol, m.p.: 165° C.
1,1-bis-(4-chlorophenyl)-2-(imidazol-1-yl)-ethan-1-ol, m.p.: 200° C.

EXAMPLE 4

5.35 g of magnesium chips are introduced into 50 ml of diethyl ether, followed by the dropwise addition at boiling temperature of 39.1 g of 1-bromo-4-chlorobenzene dissolved in 250 ml of diethyl ether. On completion of the addition, 22.4 g of trichloroacetophenone into 50 ml of diethyl ether are immediately added dropwise at room temperature. This is followed by decomposition with aqueous ammonium chloride solution. The organic phase is separated off, washed until neutral, dried over sodium sulphate and concentrated in vacuo. The reaction product (oil) is mixed with 68 g of imidazole, melted and stirred for 2 hours at 120° C. The melt is cooled, taken up in methylene chloride and washed with water, dried over sodium sulphate and concentrated. The residue is recrystallised from ethanol, giving 11.3 g of base melting at 263°-265° C.

The base is dissolved in chloroform and the nitrate produced by adding 100% $HNO_3$ dissolved in diethyl ether. Recrystallisation from isopropyl ether/isopropanol gives 8.3 g of 1-(4-chlorophenyl)-1-(2,4-dichlorophenyl)-2-(imidazol-1-yl)-ethan-1-ol nitrate melting at 217°-218° C.

EXAMPLES 5 TO 7

The following compounds were produced as in Example 4:
1-(4-chlorophenyl)-1-(2,4-dichlorophenyl)-2-(2-isopropylimidazol-1-yl)-ethan-1-ol nitrate, m.p.: 205°-207° C.
1-(4-chlorophenyl)-1-(2,4-dichlorophenyl)-2-(2-methylimidazol-1-yl)-ethan-1-ol nitrate, m.p.: 229°-231° C.
1-(3-chlorophenyl)-2-(2,4-dichlorophenyl)-3-(imidazol-1-yl)-ethan-1-ol, m.p.: 252° C.

EXAMPLE 8

5.35 g of magnesium chips in 50 ml of diethyl ether are reacted at boiling temperature with 32.2 g of p-chlorobenzyl chloride dissolved in 200 ml of diethyl ether. 18.9 g of 2,2'-dichloroacetophenone dissolved in 150 ml of diethyl ether are then added dropwise to the resulting solution. After decomposition with aqueous ammonium chloride solution, the organic phase is concentrated in vacuo after washing with water and drying over sodium sulphate. The residue is dissolved in 75 ml of dimethyl formamide and reacted at room temperature with a solution of sodium imidazole prepared from 3 g of sodium in 36 ml of methanol and 15 g of imidazole. After heating for 90 minutes to 50° C., the solvent is distilled off in vacuo, the product is washed with water and ether and then dissolved in chloroform. The addition of an etherial nitric acid solution gives 1,2-bis-(4-chlorophenyl)-3-(imidazol-1-yl)-propan-2-ol nitrate melting at 207° to 208° C.

EXAMPLE 9

5.35 g of magnesium chips in 50 ml of ether are reacted at boiling temperature with 39.1 g of 2,4-dichlorobenzyl chloride dissolved in 200 ml of diethyl ether. 22.4 g of 2,2',4'-trichloroacetophenone dissolved in 150 ml of diethyl ether are added dropwise to the resulting solution. After decomposition with aqueous ammonium chloride solution, the organic phase is separated off and dried over sodium sulphate. After concentration in vacuo, the residue is added to a melt of 68.1 g of imidazole and reacted for 2 hours with stirring at 120° C. After cooling, first water and then methylene chloride are added to the reaction mixture. The white residue is filtered off, dissolved under heat in chloroform and the nitrate is precipitated with 100% nitric acid dissolved in dimethyl ether.

Recrystallisation from isopropanol/ethylacetate gives 33.5 g of 1,2-bis-(2,4-dichlorophenyl)-3-(imidazol-1-yl)-propan-2-ol-nitrate melting at 170° to 172° C.

EXAMPLE 10

(a) 5.35 g of magnesium chips and a little iodine are added to a solution of 3 g of 2,6-dichlorobenzyl chloride in 20 ml of diethyl ether. After brief heating, the reaction begins, after which another 36.1 g of 2,6-dichlorobenzyl chloride dissolved in 230 ml of diethyl ether are added dropwise at boiling temperature. A solution of 18.9 g of 2,2',4'-trichloroacetophenone in 150 ml of ether is then added dropwise, and the mixture left to react for 2 hours. The reaction mixture is then treated with an aqueous ammonium chloride solution, the ethereal phase is dried over sodium sulphate and concentrated in vacuo. Treatment of the solid residue with isopropyl ether gives 19.3 g of 1-(2,6-dichlorophenyl)-2-(2,4-dichlorophenyl)-3-chloropropan-2-ol melting at 117° C.

(b) 3.85 g of 1-(2,6-dichlorophenyl)-2-(2,4-dichlorophenyl)-3-chloropropan-2-ol are reacted for 2 hours at 120° C. with 6.8 g of imidazole. Working up in accordance with Example 8, followed by recrystallisation from isopropanol, gives 3.2 g of 1-(2,6-dichlorophenyl)-2-(2,4-dichlorophenyl)-3-(imidazol-1-yl)propan-2-ol nitrate melting at 221° C.

EXAMPLE 11

32.2 g of 2-chlorobenzyl chloride dissolved in 450 ml of diethyl ether are added dropwise at boiling temperature to 5.35 g of magnesium chips in 50 ml of diethyl ether. On completion of the reaction, 18.6 g of 2-chloro-4'-methoxyacetophenone dissolved in 150 ml of tetrahydrofuran are added. After decomposition with aqueous ammonium chloride solution, the organic phase is separated off, washed until neutral and dried over sodium sulphate. After concentration in vacuo, the residue is dissolved in 75 ml of dimethyl formamide and stirred overnight at room temperature with a solution of sodium imidazole in 75 ml of dimethyl formamide prepared from 3 g of sodium in 50 ml of methanol and 15 g of imidazole. The solvent is distilled off in vacuo, the residue is dissolved in chloroform, washed with water and dried over sodium sulphate.

A white nitrate is precipitated on the addition of ethereal nitric acid. Recrystallisation twice from n-propanol and once from ethanol gives 8.7 g of 1-(2-chlorophenyl)-2-(4-methoxyphenyl)-3-(imidazol-1-yl)-propan-2-ol nitrate melting at 167° C.

EXAMPLE 12

5.35 g of magnesium chips are introduced into 50 ml of diethyl ether, followed by the dropwise addition at boiling temperature of 39.1 g of 2,4-dichlorobenzyl chloride dissolved in 250 ml of diethyl ether. On completion of the addition, 17.3 g of 2-chloro-4'-fluoroacetophenone dissolved in 250 ml of diethyl ether are immediately added dropwise at boiling temperature. After decomposition with aqueous ammonium chloride solution, the organic phase is separated off, washed until neutral, dried over sodium sulphate and concentrated in vacuo. The reaction product is mixed with 68 g of imidazole, melted and stirred for 2 hours at 120° C. The melt is cooled, poured onto ice/water and extracted by shaking with methylene chloride. The organic phase is washed free from imidazole, dried over sodium sulphate and concentrated. The residue is recrystallised from methanol, giving 14.3 g of 1-(2,4-dichlorophenyl)-2-(4-fluorophenyl)-3-(imidazol-1-yl)-propan-2-ol melting at 178°-179° C.

The base is dissolved in chloroform and the nitrate is precipitated with 100% nitric acid dissolved in diethyl ether. Recrystallisation from isopropyl alcohol gives 14.6 g of 1-(2,4-dichlorophenyl)-2-(4-fluorophenyl)-3-(imidazol-1-yl)-propan-2-ol nitrate melting at 184° to 185° C.

EXAMPLES 13 TO 55

The following compounds were produced as in Examples 8 to 12:
(13) 1,2-diphenyl-3-(imidazol-1-yl)-propan-2-ol, m.p.: 210° C.
(14) 1,2-diphenyl-3-(imidazol-1-yl)-propan-2-ol nitrate, m.p.: 192° C.
(15) 1-phenyl-2-(4-chlorophenyl)-3-(imidazol-1-yl)-propan-2-ol nitrate, m.p.: 190° C.
(16) 1-phenyl-2-(4-bromophenyl)-3-(imidazol-1-yl)-propan-2-ol nitrate, m.p.: 201° C.
(17) 1-phenyl-2-(2,4-dichlorophenyl)-3-(imidazol-1-yl)-propan-2-ol nitrate, m.p.: 174° C.
(18) 1-phenyl-2-(2-bromo-4-chlorophenyl)-3-(imidazol-1-yl)-propan-2-ol, m.p.: 172° C.
(19) 1-phenyl-2-(2-bromo-4-chlorophenyl)-3-(imidazol-1-yl)-propan-2-ol nitrate, m.p.: 184° C.
(20) 1-(2-chlorophenyl)-2-phenyl-3-(imidazol-1-yl)-propan-2-ol, m.p.: 186° C.
(21) 1-(2-chlorophenyl)-2-phenyl-3-(imidazol-1-yl)-propan-2-ol nitrate, m.p.: 196° C.
(22) 1-(2-chlorophenyl)-2-(2,4-dichlorophenyl)-3-(imidazol-1-yl)-propan-2-ol, m.p.: 203° C.
(23) 1-(2-chlorophenyl)-2-(2,4-dichlorophenyl)-3-(imidazol-1-yl)-propan-2-ol nitrate, m.p.: 159° C.
(24) 1-(2-chlorophenyl)-2-(2-bromo-4-chlorophenyl)-3-(imidazol-1-yl)-propan-2-ol, m.p.: 209° C.
(25) 1-(2-chlorophenyl)-2-(2-bromo-4-chlorophenyl)-3-(imidazol-1-yl)-propan-2-ol nitrate, m.p.: 163° C.
(26) 1-(2-chlorophenyl)-2-(4-chloro-2-methylphenyl)-3-(imidazol-1-yl)-propan-2-ol nitrate, m.p.: 165° C.
(27) 1-(4-chlorophenyl)-2-phenyl-3-(imidazol-1-yl)-propan-2-ol, m.p.: 190° C.
(28) 1-(4-chlorophenyl)-2-phenyl-3-(imidazol-1-yl)-propan-2-ol nitrate, m.p.: 189° C.
(29) 1-(4-chlorophenyl)-2-(4-bromophenyl)-3-(imidazol-1-yl)-propan-2-ol nitrate, m.p.: 204° C.
(30) 1-(4-chlorophenyl)-2-(2,4-dichlorophenyl)-3-(imidazol-1-yl)-propan-2-ol hydrochloride, m.p.: 110° C. (decomp.)
(31) 1-(4-chlorophenyl)-2-(2-bromo-4-chlorophenyl)-3-(imidazol-1-yl)-propan-2-ol, m.p.: 221° C.
(32) 1-(4-chlorophenyl)-2-(2-bromo-4-chlorophenyl)-3-(imidazol-1-yl)-propan-2-ol nitrate, m.p.: 160° C.
(33) 1-(2,4-dichlorophenyl)-2-phenyl-3-(imidazol-1-yl)-propan-2-ol, m.p.: 219° C.
(34) 1-(2,4-dichlorophenyl)-2-phenyl-3-(imidazol-1-yl)-propan-2-ol nitrate, m.p.: 218° C.
(35) 1-(2,4-dichlorophenyl)-2-(2-bromo-4-chlorophenyl)-3-(imidazol-1-yl)-propan-2-ol, m.p.: 205° C.
(36) 1-(2,4-dichlorophenyl)-2-(2-bromo-4-chlorophenyl)-3-(imidazol-1-yl)-propan-2-ol nitrate, m.p.: 175° C.
(37) 1-(2,4-dichlorophenyl)-2-(4-methoxyphenyl)-3-(imidazol-1-yl)-propan-2-ol nitrate, m.p.: 202° C.
(38) 1-(3,4-dichlorophenyl)-2-(4-methoxyphenyl)-3-(imidazol-1-yl)-propan-2-ol, m.p.: 124° C.
(39) 1-(3,4-dichlorophenyl)-2-(4-methoxyphenyl)-3-(imidazol-1-yl)-propan-2-ol nitrate, m.p.: 144° C.
(40) 1-(3,4-dichlorophenyl)-2-(2-bromo-4-chlorophenyl)-3-(imidazol-1-yl)-propan-2-ol, m.p.: 190° C.
(41) 1-(3,4-dichlorophenyl)-2-(2-bromo-4-chlorophenyl)-3-(imidazol-1-yl)-propan-2-ol nitrate, m.p.: 202° C.

(42) 1-(2,6-dichlorophenyl)-2-phenyl-3-(imidazol-1-yl)-propan-2-ol nitrate, m.p.: 174° C.
(43) 1-(2,6-dichlorophenyl)-2-(2-bromo-4-chlorophenyl)-3-(imidazol-1-yl)-propan-2-ol, m.p.: 208° C.
(44) 1-(2,6-dichlorophenyl)-2-(2-bromo-4-chlorophenyl)-3-(imidazol-1-yl)-propan-2-ol nitrate, m.p.: 222° C.
(45) 1-(4-methylphenyl)-2-(2,4-dichlorophenyl)-3-(imidazol-1-yl)-propan-2-ol nitrate, m.p.: 165° C.
(46) 1-(2,4-dichlorophenyl)-2-(3,4-dichlorophenyl)-3-(imidazol-1-yl)-propan-2-ol nitrate, m.p.: 189° C.
(47) 1-(2,4-dichlorophenyl)-2-(4-chloro-2-methylphenyl)-3-(imidazol-1-yl)-propan-2-ol nitrate, m.p.: 150° C.
(48) 1-(4-chlorophenyl)-2-(4-methoxyphenyl)-3-(imidazol-1-yl)-propan-2-ol nitrate, m.p.: 205° C.
(49) 1-(2,4-dichlorophenyl)-2-(4-fluorophenyl)-3-(imidazol-1-yl)-propan-2-ol nitrate, m.p.: 185° C.
(50) 1-(2,6-dichlorophenyl)-2-(4-methoxyphenyl)-3-(imidazol-1-yl)-propan-2-ol nitrate, m.p.: 172° C.
(51) 1-(2,4-dichlorophenyl)-2-(4-chlorophenyl)-3-(imidazol-1-yl)-propan-2-ol hydrochloride, m.p.: approx. 200° C.
(52) 1-(2,4-dichlorophenyl)-2-(4-iodophenyl)-3-(imidazol-1-yl)-propan-2-ol nitrate, m.p.: approx. 112° C.
(53) 1-(3,4-dichlorophenyl)-2-(4-chlorophenyl-2-methylphenyl)-3-(imidazol-1-yl)-propan-2-ol nitrate, m.p.: 168° C.
(54) 1,2-bis-(2,4-dichlorophenyl)-2-(2-methylimidazol-1-yl)-propan-2-ol, m.p.: 222° C.
(55) 1,2-bis-(2,4-dichlorophenyl)-2-(2-isopropylimidazol-1-yl)-propan-2-ol nitrate, m.p.: approx. 76° C.

EXAMPLE 56

Tablet containing 250 mg of active principle

| | |
|---|---|
| Active principle of Example 30 (1-(4-chlorophenyl)-2-(2,4-dichlorophenyl)-3-(imidazol-1-yl)-propan-2,ol hydrochloride) | 250 g |
| Potato starch | 100 g |
| Lactose | 50 g |
| Gelatin solution (4%) | approx. 45 g |
| Talcum | 10 g |
| 1000 tablets = | approx. 410 g |

Preparation

The finely powdered active principle, potato starch and lactose are mixed. The mixture is moistened with approximately 45 g of 4% gelatin solution, granulated into fine grains and dried. The dry granulate is sifted, mixed with 10 g of talcum and pressed into tablets on a rotary tabletting machine. The tablets are introduced into tightly closing containers of polypropylene.

EXAMPLE 57

Cream containing 2% of active principle

| | |
|---|---|
| Active principle of Example 30 (1-(4-chlorophenyl)-2-(2,4-dichlorophenyl)-3-(imidazol-1-yl)-propan-2-ol hydrochloride | 2.0 g |
| Glycerol monostearate | 10.0 g |
| Cetyl alcohol | 5.0 g |
| Polyethylene glycol-400-stearate | 10.0 g |
| Polyethylene glycol sorbitan monostearate | 10.0 g |
| Propylene glycol | 6.0 g |
| p-Hydroxybenzoic acid methyl ester | 0.2 g |
| Demineralised water | ad 100.0 g |

Preparation

The very finely powdered active principle is suspended in the propylene glycol and the suspension is stirred into a melt heated to 65° C. of glycerol monostearate, cetyl alcohol, polyethylene glycol-400-stearate and polyethylene glycol sorbitan monostearate. A solution of the p-hydroxybenzoic acid methyl ester in water heated to 70° C. is emulsified into the resulting mixture. After cooling, the cream is homogenised in a colloid mill and filled into tubes.

EXAMPLE 58

Powder containing 2% of active principle

| | |
|---|---|
| Active principle of Example 30 (1-(4-chlorophenyl)-2-(2,4-dichlorophenyl)-3-(imidazol-1-yl)-propan-2-ol hydrochloride) | 2.0 g |
| Zinc oxide | 10.0 g |
| Magnesium oxide | 10.0 g |
| Highly disperse silicon oxide | 2.5 g |
| Magnesium stearate | 1.0 g |
| Talcum | 74.5 g |

Preparation

The active principle is micronised in an air jet mill and mixed homogeneously with the other constituents. The mixture is sifted through a number 7 sieve and filled into polyethylene containers with a sprinkler cap.

What we claim is:

1. A basic imidazolyl alcohol corresponding to the general formula

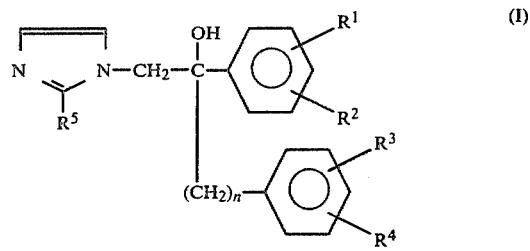

in which
R$^1$, R$^2$, R$^3$ and R$^4$, which may be the same or different, each represent a member selected from the group consisting of hydrogen, the halogen atoms, the lower alkyl groups with 1 to 4 carbon atoms and the lower alkoxy groups with 1 to 4 carbon atoms, R$^5$ represents a member selected from the group consisting of hydrogen and the lower alkyl groups with 1 to 3 carbon atoms and
n is an integer selected from the group consisting of 0 and 1, and the pharmacologically compatible acid addition salts thereof.

2. A basic imidazolyl alcohol as claimed in claim 1 wherein n is 1.

3. A basic imidazolyl alcohol as claimed in claim 2 wherein R$^1$, R$^2$, R$^3$ and R$^4$, which may be the same or different, each represent a member selected from the group consisting of hydrogen, fluorine, bromine, chlorine, methyl and methoxy.

4. 1-Phenyl-2-(4-chlorophenyl)-3-(imidazol-1-yl)-propan-2-ol and its pharmacologically compatible acid addition salts.

5. 1-Phenyl-2-(2,4-dichlorophenyl)-3-(imidazol-1-yl)-propan-2-ol and its pharmacologically compatible acid addition salts.

6. 1-(2-Chlorophenyl)-2-(2,4-dichlorophenyl)-3-(imidazol-1-yl)-propan-2-ol and its pharmacologically compatible acid addition salts.

7. 1-(2-Chlorophenyl)-2-(4-chloro-2-methylphenyl)-3-(imidazol-1-yl)-propan-2-ol and its pharmacologically compatible acid addition salts.

8. 1-(4-Chlorophenyl)-2-phenyl-3-(imidazol-1-yl)-propan-2-ol and its pharmacologically compatible acid addition salts.

9. 1,2-Bis-(4-chlorophenyl)-3-(imidazol-1-yl)-propan-2-ol and its pharmacologically compatible acid addition salts.

10. 1-(4-Chlorophenyl)-2-(2,4-dichlorophenyl)-3-(imidazol-1-yl)-propan-2-ol and its pharmacologically compatible acid addition salts.

11. 1-(2,4-Dichlorophenyl)-2-(4-chlorophenyl)-3-(imidazol-1-yl)-propan-2-ol and its pharmacologically compatible acid addition salts.

12. 1,2-Bis-(2,4-dichlorophenyl)-3-(imidazol-1-yl)-propan-2-ol and its pharmacologically compatible acid addition salts.

13. 1-(2,4-Dichlorophenyl)-2-(2-bromo-4-chlorophenyl)-3-(imidazol-1-yl)-propan-2-ol and its pharmacologically compatible acid addition salts.

14. 1-(2,4-Dichlorophenyl)-2-(3,4-dichlorophenyl)-3-(imidazol-1-yl)-propan-2-ol and its pharmacologically compatible acid addition salts.

15. 1-(4-Methylphenyl)-2-(2,4-dichlorophenyl)-3-(imidazol-1-yl)-propan-2-ol and its pharmacologically compatible acid addition salts.

16. The method for the treatment of generalized or local infections caused by fungi and yeasts comprising orally administering to the mammal to be treated a compound according to claim 1 in an amount ranging from 0.5 to 100 mg./kg. of body weight.

17. The method for the external treatment of local infections caused by fungi and yeasts comprising treating the infected part of the infected mammal with an ointment, creme, emulsion, solution or powder containing 0.1 to 10% by weight of a compound according to claim 1.

* * * * *